US012564444B2

(12) United States Patent
Junio et al.

(10) Patent No.: US 12,564,444 B2
(45) Date of Patent: Mar. 3, 2026

(54) BONE ENTRY POINT VERIFICATION SYSTEMS AND METHODS

(71) Applicant: Mazor Robotics Ltd., Caesarea (IL)

(72) Inventors: Dany Junio, Tel Aviv-Jaffa (IL); Moshe Shoham, Hoshaya (IL)

(73) Assignee: Mazor Robotics Ltd., Caesarea (IL)

( * ) Notice: Subject to any disclaimer, the term of this patent is extended or adjusted under 35 U.S.C. 154(b) by 1075 days.

(21) Appl. No.: 17/575,245

(22) Filed: Jan. 13, 2022

(65) Prior Publication Data

US 2022/0241016 A1     Aug. 4, 2022

Related U.S. Application Data

(60) Provisional application No. 63/144,118, filed on Feb. 1, 2021.

(51) Int. Cl.
A61B 34/10          (2016.01)
A61B 17/16          (2006.01)
                (Continued)

(52) U.S. Cl.
CPC .......... A61B 34/10 (2016.02); A61B 17/1615 (2013.01); A61B 34/20 (2016.02);
                (Continued)

(58) Field of Classification Search
CPC ......... A61B 34/10; A61B 34/20; A61B 34/30; A61B 34/25; A61B 2034/101;
                (Continued)

(56) References Cited

U.S. PATENT DOCUMENTS

| | | |
|---|---|---|
| 8,221,427 B2 | 7/2012 | Roh |
| 10,413,334 B2 | 9/2019 | Warren et al. |
| (Continued) | | |

FOREIGN PATENT DOCUMENTS

| | | |
|---|---|---|
| JP | 2019-202130 | 11/2019 |
| WO | WO 2020/105049 | 5/2020 |
| (Continued) | | |

OTHER PUBLICATIONS

Baka et al. "Ultrasound aided vertebral level localization for lumbar surgery," IEEE Transactions on Medical Imaging, Oct. 2017, vol. 36, No. 10, pp. 2138-2147.
                (Continued)

*Primary Examiner* — Marcela I. Shirsat
(74) *Attorney, Agent, or Firm* — Sheridan Ross P.C.

(57)          ABSTRACT

A method for verifying a bone entry point includes receiving a surgical plan that defines a target bone entry point and a first portion of a bone surface at least partially surrounding the target bone entry point; positioning an imaging device near an identified bone entry point; receiving, from the imaging device, an image of a second portion of the bone surface surrounding the identified bone entry point; comparing at least one feature of the first portion to at least one feature of the second portion to quantify a degree of similarity therebetween; and generating, when the quantified degree of similarity between the first portion and the second portion exceeds a threshold, a confirmation.

17 Claims, 3 Drawing Sheets

300

304 — Receive a surgical plan that defines a target entry point and one or more first features of anatomical tissue around a target entry point 308 — Position an imaging device near an identified entry point of the anatomical tissue 312 — Receive an image of one or more second features of the anatomical tissue around the identified entry point 316 — Determine whether the one or more first features match the one or more second features and quantify any difference 320 — When the one or more first features match the one or more second features, generate a confirmation that the identified entry point matches the target entry point 324 — When the one or more first features do not match the one or more second features, generate an alert that the identified entry point does not match the target entry point 328 — Perform a surgical procedure on the anatomical tissue using a surgical tool

(51) Int. Cl.

| | |
|---|---|
| *A61B 34/00* | (2016.01) |
| *A61B 34/20* | (2016.01) |
| *A61B 34/30* | (2016.01) |
| *A61B 90/00* | (2016.01) |

(52) U.S. Cl.
CPC ... *A61B 2034/101* (2016.02); *A61B 2034/105* (2016.02); *A61B 2034/107* (2016.02); *A61B 2034/2055* (2016.02); *A61B 2034/2063* (2016.02); *A61B 2034/2065* (2016.02); *A61B 2034/2068* (2016.02); *A61B 34/25* (2016.02); *A61B 2034/252* (2016.02); *A61B 2034/258* (2016.02); *A61B 34/30* (2016.02); *A61B 90/37* (2016.02); *A61B 2090/3735* (2016.02); *A61B 2090/374* (2016.02); *A61B 2090/376* (2016.02); *A61B 2090/3762* (2016.02); *A61B 2090/3764* (2016.02)

(58) Field of Classification Search
CPC .... A61B 2034/2046; A61B 2034/2065; A61B 2034/2068; A61B 2034/105; A61B 2034/107; A61B 2034/2063; A61B 2034/2051; A61B 2034/2055; A61B 2034/252; A61B 2034/258; A61B 17/1615; A61B 90/37; A61B 2090/3735; A61B 2090/374; A61B 2090/376; A61B 2090/3762; A61B 2090/378; A61B 2090/3764
USPC .................................. 606/96, 86 R, 86 B, 97
See application file for complete search history.

(56) References Cited

U.S. PATENT DOCUMENTS

| | | | |
|---|---|---|---|
| 10,413,366 | B2 | 9/2019 | Dyer et al. |
| 10,499,961 | B2 | 12/2019 | Simon et al. |
| 10,517,681 | B2 | 12/2019 | Roh et al. |
| 10,568,694 | B2 | 2/2020 | Palma et al. |
| 10,610,378 | B2 | 4/2020 | Piron et al. |
| 10,617,324 | B2 | 4/2020 | Hunter et al. |
| 10,716,627 | B2 | 7/2020 | Sohlden et al. |
| 10,743,938 | B2 | 8/2020 | Wang et al. |
| 2006/0142657 | A1* | 6/2006 | Quaid ..................... A61B 90/37 600/424 |
| 2008/0269596 | A1* | 10/2008 | Revie ..................... A61B 90/39 705/28 |
| 2013/0218003 | A1 | 8/2013 | Rothgang et al. |
| 2015/0100067 | A1 | 4/2015 | Cavanagh et al. |
| 2015/0328004 | A1* | 11/2015 | Mafhouz ............ G05B 19/4099 700/98 |
| 2015/0366576 | A1 | 12/2015 | Liou et al. |
| 2018/0168736 | A1 | 6/2018 | Yang |
| 2018/0217734 | A1 | 8/2018 | Koenig et al. |
| 2019/0388155 | A1 | 12/2019 | Cattin et al. |
| 2020/0008878 | A1 | 1/2020 | Srimohanarajah et al. |
| 2020/0229869 | A1 | 7/2020 | Dorman |
| 2020/0253667 | A1 | 8/2020 | Fouts et al. |
| 2020/0289133 | A1* | 9/2020 | Elbanna ............. A61B 17/1615 |
| 2021/0386480 | A1* | 12/2021 | Tolkowsky ............ A61B 46/20 |
| 2022/0409291 | A1* | 12/2022 | Shochat ................. A61B 34/10 |

FOREIGN PATENT DOCUMENTS

| | | | |
|---|---|---|---|
| WO | WO 2020/109161 | 6/2020 | |
| WO | WO-2021105992 A1 * | 6/2021 | ......... A61B 17/3403 |

OTHER PUBLICATIONS

Reda et al. "Automatic pre- to intra-operative CT registration for image-guided cochlear implant surgery," IEEE Transactions on Biomedical Engineering, Nov. 2012, vol. 59, No. 11, pp. 3070-3077.
Knez et al. "Computer-Assisted Pedicle Screw Placement Planning: Towards Clinical Practice," IEEE, 2018 IEEE 15th International Symposium on Biomedical Imaging (ISBI 2018), Apr. 4-7, 2018, Washington, DC, USA, 5 pages.
"Operations and procedures, Handbook of Neurosurgery," Doctorlib, ©2015-2019, 7th edition, Chapter 7, 189 pages [retrieved online Oct. 13, 2020 from: doctorlib.info/neurosurgery/handbook-neurosurgery/ 8.html].
International Search Report and Written Opinion for International (PCT) Patent Application No. PCT/IL2022/050128, dated May 24, 2022, 15 pages.

* cited by examiner

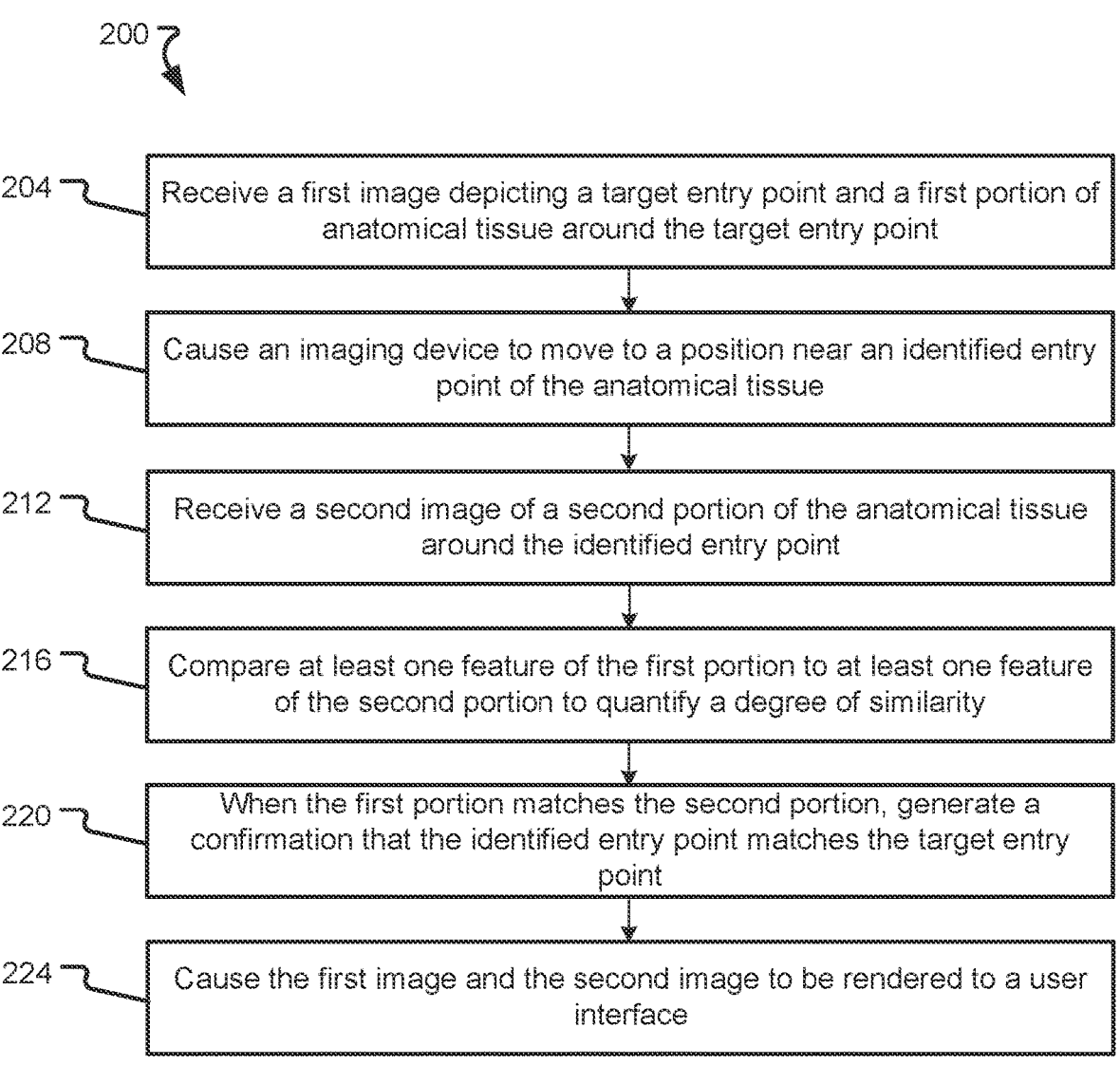

200

204 Receive a first image depicting a target entry point and a first portion of anatomical tissue around the target entry point 208 Cause an imaging device to move to a position near an identified entry point of the anatomical tissue 212 Receive a second image of a second portion of the anatomical tissue around the identified entry point 216 Compare at least one feature of the first portion to at least one feature of the second portion to quantify a degree of similarity 220 When the first portion matches the second portion, generate a confirmation that the identified entry point matches the target entry point 224 Cause the first image and the second image to be rendered to a user interface

FIG. 2

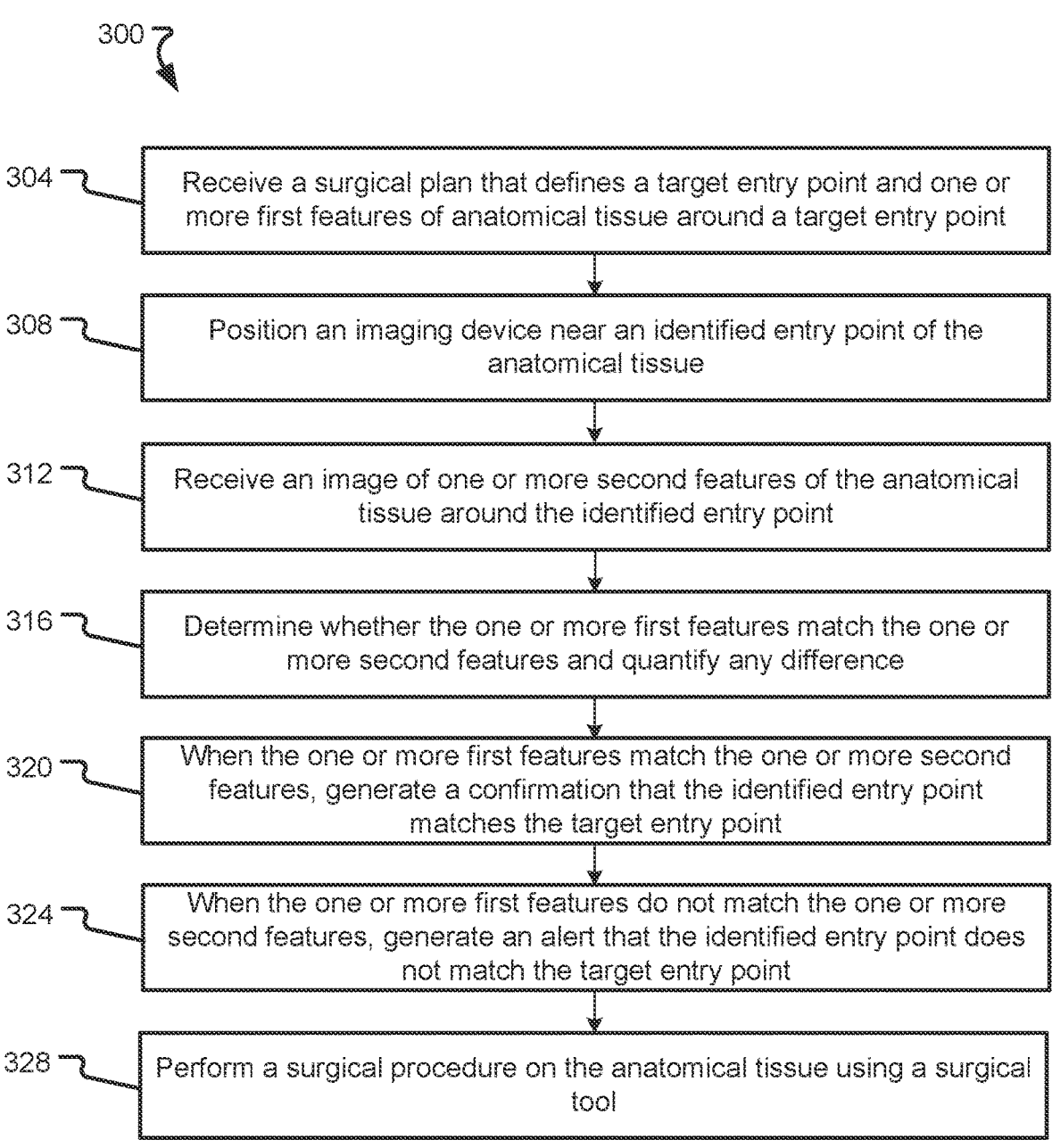

300

304 — Receive a surgical plan that defines a target entry point and one or more first features of anatomical tissue around a target entry point 308 — Position an imaging device near an identified entry point of the anatomical tissue 312 — Receive an image of one or more second features of the anatomical tissue around the identified entry point 316 — Determine whether the one or more first features match the one or more second features and quantify any difference 320 — When the one or more first features match the one or more second features, generate a confirmation that the identified entry point matches the target entry point 324 — When the one or more first features do not match the one or more second features, generate an alert that the identified entry point does not match the target entry point 328 — Perform a surgical procedure on the anatomical tissue using a surgical tool

FIG. 3

BONE ENTRY POINT VERIFICATION SYSTEMS AND METHODS

CROSS-REFERENCE TO RELATED APPLICATIONS

This application claims priority to and the benefit of U.S. Provisional Application No. 63/144,118, filed on Feb. 1, 2021, entitled "Bone Entry Point Verification Systems and Methods". The entire disclosure of the application listed above is hereby incorporated herein by reference, in its entirety, for all that it teaches and for all purposes.

FIELD

The present technology generally relates to surgical procedures, and relates more particularly to verifying surgical entry points into hard tissue.

BACKGROUND

Surgical procedures may follow a surgical plan and can be conducted autonomously or semi-autonomously. Imaging may be used to assist a surgeon or surgical robot in ensuring the success of the surgical procedure. Patient anatomy can change over time, including between capturing an image of the patient for a surgical plan and the start of the surgical procedure.

SUMMARY

Example Aspects of the Present Disclosure Include:

A method for verifying a bone entry point according to at least one embodiment of the present disclosure comprises receiving a surgical plan that defines a target bone entry point and a first portion of a bone surface at least partially surrounding the target bone entry point; positioning an imaging device near an identified bone entry point; receiving, from the imaging device, an image of a second portion of the bone surface at least partially surrounding the identified bone entry point; comparing at least one feature of the first portion to at least one feature of the second portion to quantify a degree of similarity therebetween; and generating, when the quantified degree of similarity between the first portion and the second portion exceeds a threshold, a confirmation.

Any of the aspects herein, wherein the confirmation indicates that the identified bone entry point matches the target bone entry point.

Any of the aspects herein, wherein the confirmation causes a surgical tool to drill into the identified bone entry point along a planned bone entry trajectory.

Any of the aspects herein, wherein each of the at least one feature of the first portion and the at least one feature of the second portion is a surface gradient.

Any of the aspects herein, wherein each of the at least one feature of the first portion and the at least one feature of the second portion is an anatomical landmark.

Any of the aspects herein, wherein the confirmation indicates a level of statistical certainty that the identified bone entry point matches the target bone entry point.

Any of the aspects herein, wherein the threshold is a percent similarity between the at least one feature of the first portion and the at least one feature of the second portion.

Any of the aspects herein, wherein the threshold is at least ninety-nine percent.

Any of the aspects herein, wherein the imaging device is an ultrasound probe.

Any of the aspects herein, wherein the ultrasound probe is positioned in a minimally invasive surgery (MIS) port.

Any of the aspects herein, wherein the MIS port is filled with a solution.

Any of the aspects herein, wherein the solution is water or saline.

Any of the aspects herein, wherein the MIS port is located on an upper part of a lower vertebral body.

Any of the aspects herein, wherein the imaging device is an optical imaging device.

Any of the aspects herein, wherein the target bone is a vertebra.

Any of the aspects herein, further comprising drilling into the identified bone entry point using a surgical tool.

Any of the aspects herein, wherein the positioning the imaging device near the identified bone entry point comprises orientating the imaging device substantially parallel to a planned bone entry trajectory.

A system for verifying an entry point into anatomical tissue according to at least one embodiment of the present disclosure comprises a processor; and a memory storing instructions for execution by the processor that, when executed by the processor, cause the processor to: receive a surgical plan that defines a target entry point of an anatomical tissue and comprises a first image of a first portion of the anatomical tissue near the target entry point; cause an imaging device to be positioned proximate to an identified entry point of the anatomical tissue; receive, from the imaging device, a second image of a second portion of the anatomical tissue near the identified entry point; and cause the first image and the second image to be rendered to a user interface.

Any of the aspects herein, wherein the anatomical tissue is bone.

Any of the aspects herein, wherein the imaging device is positioned in a surgical incision.

Any of the aspects herein, wherein the surgical incision comprises an MIS port.

Any of the aspects herein, wherein the image of the second portion is an ultrasound image.

Any of the aspects herein, wherein the instructions further cause the processor to: compare the first portion to the second portion.

Any of the aspects herein, wherein the comparing comprises quantifying a difference between at least one characteristic of the first portion of the anatomical tissue and at least one characteristic of the second portion of the anatomical tissue.

Any of the aspects herein, wherein the anatomical tissue is a vertebra.

Any of the aspects herein, wherein the instructions further cause the processor to: generate, when the quantified difference between the at least one characteristic of the first portion of the anatomical tissue and the at least one characteristic of the second portion of the anatomical tissue is below a threshold value, a confirmation that the identified entry point matches the target entry point.

Any of the aspects herein, wherein the positioning the imaging device near the planned entry point comprises orienting the imaging device substantially parallel to a planned entry trajectory.

A system according to at least one embodiment of the present disclosure comprises: an imaging device; a processor; and a memory storing instructions for execution by the processor that, when executed by the processor, cause the processor to: receive a surgical plan that defines a target bone entry point and a first bone contour proximate the target bone entry point; position the imaging device near an identified bone entry point; cause the imaging device to capture an image of a second bone contour proximate the identified bone entry point; determine, based on a predetermined threshold, whether the first bone contour matches the second bone contour; when the first bone contour matches the second bone contour, generate a confirmation that the identified bone entry point matches the target bone entry point; and when the first bone contour does not match the second bone contour, generate an alert that the identified bone entry point does not match the target bone entry point.

Any of the aspects herein, wherein the imaging device is an ultrasound probe.

Any of the aspects herein, wherein the imaging device is oriented substantially parallel to a planned bone entry trajectory.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 2 is a flowchart according to at least one embodiment of the present disclosure; and FIG. 3 is a flowchart according to at least one embodiment of the present disclosure;

DETAILED DESCRIPTION

Figure 1:
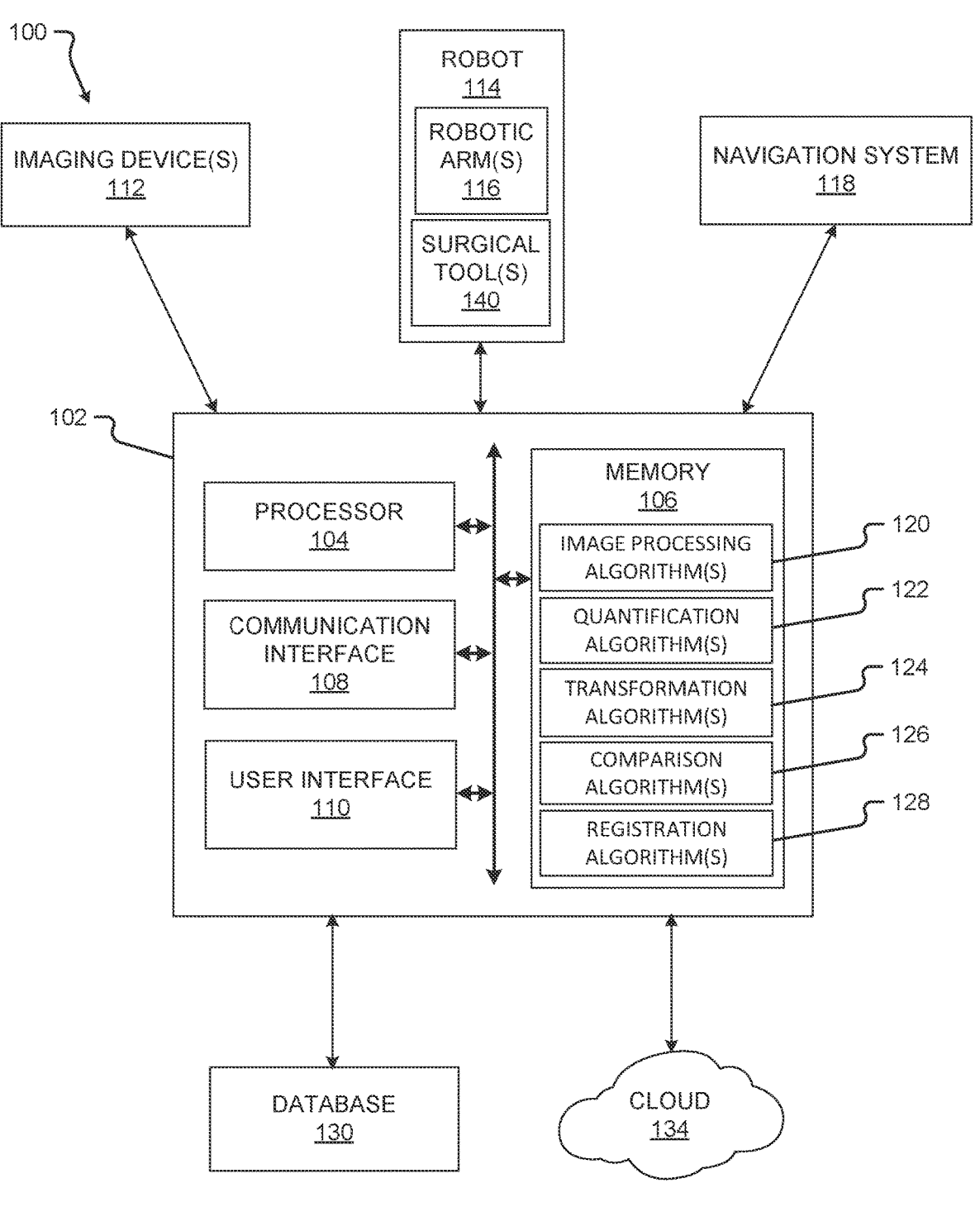
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors;

AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

When removing bone that is proximate to important patient anatomy (e.g., near blood vessels, near nerve roots, etc.) during minimally invasive surgery (MIS), the entry point and/or trajectory of a surgical tool through the entry point should be confined and accurate. The accurate entry point and/or trajectory may assist a surgeon with safe entry to the relevant patient anatomy, while also lowering the risk of patient injury and/or insufficient bone removal. Both free hand surgical techniques as well as technology assisted techniques often fail to provide real-time feedback of the entry point and/or trajectory of the surgical tool. Instead, the MIS port construct may be approved, and the surgery may proceed by assuming that the if the robot and/or navigation systems are accurate (e.g., the registration is correct) and the MIS construct is known to be rigidly positioned, the entry point and/or trajectory of the surgical tool is also correct. The position of the MIS construct may additionally or alternatively be tracked, with the assumption that the entry point and/or trajectory of the surgical tool are correct as long as the MIS construct does not change position. According to embodiments of the present disclosure, a real-time feedback mechanism to indicate whether the entry point and/or trajectory of the surgical tool is accurate may be used to reduce trajectory issues arising from, for example, tool skiving, patient movement, misaligned registration, combinations thereof, and/or the like.

A feedback mechanism according to embodiments of the present disclosure may include technology that enables intraoperative imaging the vicinity of the entry point and comparing (e.g., mapping) the image to a model (e.g., a computerized model) of the identified entry point (determined preoperatively or intraoperatively), such that the surface of the entry point may be compared to the modeled surface and the entry point can be confirmed to be correct prior to actually making such entry. A binary scoring system may be used to approve or disapprove the entry of the surgical tool into the entry point based on how closely the imaged entry point matches the model. The imaging of the vicinity of the entry point may be obtained within the MIS cut or incision and may be obtained using an imaging device configured to obtain images in low light environments (e.g., within an internal cavity of the human body). The imaging device may utilize, for example, RGB/CCD visual light in combination with relevant lighting, coded light, laser patterns, LIDAR, ultrasound, combinations thereof, and/or the like. The imaging may occur near the entry point at various angles (including, e.g., parallel or perpendicular to the trajectory of the surgical tool into the bone).

Embodiments of the present disclosure provide technical solutions to one or more of the problems of verifying the entry point of a surgical tool into an anatomical tissue (e.g., bone); avoiding misaligned trajectory issues arising from tool skiving, patient movement, misaligned or incorrect/inaccurate registration, combinations thereof, and/or the like; and/or lack of real-time feedback regarding the entry point and/or trajectory of a surgical tool into anatomical tissue.

Turning first to FIG. 1, a block diagram of a system 100 according to at least one embodiment of the present disclosure is shown. The system 100 may be used to verify the entry point and/or trajectory of a surgical tool into anatomical tissue (e.g., soft tissue, bone, etc.) and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200 and/or 300 described herein, or of any other methods. The memory 106 may store, for example, one or more image processing algorithms 120, one or more quantification algorithms 122, one or more transformation algorithms 124, one or more comparison algorithms 126, and/or one or more registration algorithms 128. Such instructions or algorithms may, in some embodiments, be organized into one or more applications, modules, packages, layers, or engines. The algorithms and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the computing device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner or probe (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116 and one or more surgical tools 140. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm(s) 116, may have, for example, one, two, three, four, five, six, seven, or more degrees of freedom. Further, each robotic arm 116 may be positioned or positionable in any pose, plane, and/or focal point. The pose includes a position and an orientation. As a result, an imaging device 112, surgical tool 140, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116 and/or a surgical tool 140 held by or otherwise affixed to the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools 140 (or, more particularly, to track a pose of a navigated tracker attached, directly or indirectly, in fixed relation to the one or more of the foregoing).

The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The one or more surgical tools 140 may be configured to perform a surgery or surgical procedure or task and/or to assist a surgeon in performing the same. The surgical tool 140 may have a proximal end (e.g., an end away from or not contacting a patient) which may be affixed to the robotic arm 116. A distal end of the surgical tool (e.g., an end positioned on, within, or closest to the patient) may be configured to facilitate a surgery or surgical procedure or task. For example, the distal end may be outfitted with a tool bit (e.g., a saw, a drill bit, a burr, a shaver, a scalpel, a ream, a tap, etc.) to, for example, drill into anatomical tissue. In some embodiments, the surgical tool may comprise more than one tool bit, and/or may be configured to accept more than one tool bit (e.g., so that the tool bit can be changed, whether preoperatively, intraoperatively, or both). In still other embodiments, a robotic arm 116 may be configured to select different surgical tools 140 for different surgical tasks, or an operator of a robot 114 may secure different surgical tools 140 to the robotic arm 116 in preparation for different surgical tasks.

In some embodiments, the activation of the surgical tool (e.g., the application of power to the tool, or the switching of the surgical tool from a non-operating state to an operating state) may be controlled and/or monitored by the system 100 and/or components thereof (e.g., computing device 102). In such embodiments, the system 100 may automatically disable the surgical tool 140 until the system 100 receives a confirmation (e.g., an electronic signal) indicating that the surgery or surgical procedure is permitted to proceed.

The system 100 or similar systems may be used, for example, to carry out one or more aspects of any of the methods 200 and/or 300 described herein. The system 100 or similar systems may also be used for other purposes.

FIG. 2 depicts a method 200 that may be used, for example, to verify an entry point into anatomical tissue and/or to generate a confirmation that the entry point into the anatomical tissue is accurate with respect to a preoperative plan. Generally speaking, the method 200 provides for comparing a portion of anatomical tissue surrounding or otherwise proximate to a target entry point (as identified in a preoperative image or model) with a portion of anatomical tissue surrounding or otherwise proximate to an identified entry point where a surgical tool is about to enter an anatomical element (as identified in an intraoperative image). If the comparing results in a determination of a match between one or more of an outline, geometric form, contour, surface, edge, and/or gradient of the two portions of anatomical tissue, as depicted in the two images, then the identified entry point is treated as being the same as the target entry point. If the comparing results in a negative match determination, then the identified entry point is treated as being different than the target entry point (which, in turn, means that the target entry point has not yet been correctly located).

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing instructions stored in a memory such as the memory 106. The instructions may correspond to one or more steps of the method 200 described below. The instructions may cause the processor to execute one or more algorithms, such as an image processing algorithm 120, a quantification algorithm 122, a transformation algorithm 124, a comparison algorithm 126, and/or a registration algorithm 128.

The method 200 comprises receiving a first image depicting or otherwise identifying a target entry point and a first portion of anatomical tissue around the target entry point (step 204). The target entry point may be a designated location for entry into the anatomical tissue by a surgical tool. The target entry point may be determined by a surgical or preoperative plan, a surgeon, and/or combinations thereof, and may be the preferred, ideal, or otherwise modeled/simulated entry point for a distal end (e.g., cutting end) of a surgical tool. The target entry point may vary depending on the type of surgery, availability of surgical tools, level of autonomy (e.g., manual, semi-autonomous, autonomous, etc.) associated with the surgery, and/or the like. For example, the target entry point may be on a surface of a bone, such as a vertebra.

The target entry point may be associated with a particular trajectory, which trajectory may depend on information about the bone and/or information about the surgical tool being used. A particular trajectory associated with a given target entry point for a drill bit may be based, for example, on the type, size, and/or position of surgical drill bit used. Embodiments of the present disclosure may be utilized not only to verify that an identified entry point matches a predetermined target entry point, but also that an intended trajectory matches a predetermined trajectory. This may be accomplished, for example, by comparing a first portion of anatomical tissue surrounding or otherwise proximate to a predetermined target entry point, as seen from the predetermined trajectory, with a second portion of anatomical tissue surrounding or otherwise proximate to the identified entry point, as seen from the intended trajectory. If the first portion of anatomical tissue as seen from the predetermined trajectory matches the second portion of anatomical tissue as seen from the intended trajectory, then the intended trajectory can be confirmed to match the predetermined trajectory.

As noted above, the received image may depict or otherwise illustrate a first portion of anatomical tissue (e.g., a portion of a vertebra or other bone) around the target entry point. The received image of the first portion of the anatomical tissue may include or show information directed to one or more of an outline, geometric form, surface, edge, gradient, contour, and/or the like of the anatomical tissue around the target entry point. The image may depict a varying amount of the anatomical tissue around the target entry point. For example, the image may depict a percentage of the anatomical tissue (e.g., 1%, 2%, 5%, 10%, 25%, 50%, 75%, 90%, 100%) surrounding the target entry point depending on, for example, surgical procedure, anatomical tissue type, and/or the like. In some embodiments, the anatomical tissue may be an organ and the image may depict only a portion thereof that is relevant to the surgical procedure. In some embodiments, the anatomical tissue may be located proximate to the target entry point. For instance, the anatomical tissue may be a known distance from the target entry point. In still further embodiments, the anatomical tissue may appear as or be a prominent, distinct, or otherwise recognizable landmark, figure, shape, and/or shade at or proximate to the target entry point in the received image.

In some embodiments, the image depicting the first portion of the anatomical tissue may be captured preoperatively (e.g., before surgery), and may be stored in a system (e.g., a system 100) and/or one or more components thereof (e.g., a database 130, a memory 106, etc.). In some embodiments, the image may show a simulated anatomical tissue based on data obtained from preoperative imaging (e.g., a CT scan, an X-ray, etc.) and/or patient data (e.g., patient history). In at least one embodiment, the received image may depict one or more views of a vertebra (e.g., a lumbar vertebra). In this embodiment, the surgery or surgical procedure may be performed on the vertebra, with a surgical tool (e.g., a surgical tool 140) operating autonomously or semi-autonomously to drill and/or insert screws (e.g., pedicle screws) into the vertebra of a patient.

In some embodiments, the image may depict one or more poses (e.g., positions and orientations) of the first portion of the anatomical tissue. For instance, the anatomical tissue may be a vertebra, and the target entry point may be a location on the vertebra. The first image may depict multiple surfaces of the vertebra and/or the immediate vicinity of the vertebra, or of the contour of the vertebra in the vicinity of the target entry point. As previously noted, the first image may be a rendering or computerized model of a portion of the anatomical tissue around the target entry point. For instance, one or more algorithms may be used to generate an image of the first portion of the anatomical tissue. The one or more algorithms may be artificial intelligence (AI) or machine learning (e.g., deep learning) algorithms that generate models of anatomical tissue after receiving as input, for example, patient medical records, type of planned surgical procedure, surgical instrumentation required for the surgical procedure, previously captured images or scans of the anatomical tissue (e.g., CT scans, X-rays, MRI scans, ultrasound images, etc.), combinations thereof, and/or the like.

The method 200 also comprises causing an imaging device to move to a position near an identified entry point of the anatomical tissue (step 208). The causing may comprise controlling a robotic arm (e.g., a robotic arm 116) to which the imaging device is attached. The imaging device may be any imaging device discussed herein (e.g., an imaging device 112), though the imaging device may be an imaging device not specifically mentioned herein. The imaging device may be controlled, navigated, or otherwise manipulated using a computing device such as a computing device 102, a processor such as a processor 104, a navigation system such as a navigation system 118, and/or combinations thereof. The imaging device may be oriented relative to an identified entry point of the anatomical tissue. For example, the imaging device may be aligned in a parallel orientation relative to a planned trajectory of a distal end of the surgical tool. In some embodiments, the imaging device may be oriented in the same pose as the surgical tool would be when performing the operation. In other words, the imaging device may be positioned such that the imaging device can capture images that depict a similar or the same trajectory as the distal end of the surgical tool when performing the surgery or surgical procedure relative to the identified entry point. In other embodiments, the imaging device may be oriented perpendicular to the surgical tool. The perpendicular orientation may permit the imaging device to capture image data associated with the operation of the surgical tool (e.g., capturing images as the surgical tool drilling into an anatomical element).

In some embodiments, the imaging device may be positioned partially or fully within the patient, an MIS port, and incision, combinations thereof, and/or the like. In one embodiment, the imaging device may be an ultrasound probe positioned within an MIS port (which is in turn positioned within an incision). In this embodiment, the MIS port may be filled with a fluid (e.g., water, saline, combinations thereof, etc.) such that the fluid fills any otherwise empty space between the ultrasound probe and the imaged anatomical element (e.g., a vertebra and surrounding tissue), which may be necessary to obtain ultrasound images of the target entry point. The particular location of the MIS port is in no way limiting, and the MIS port may be constructed or otherwise provided on different areas of the patient depending on, for example, the type of surgery or surgical procedure being conducted, the availability of surgical tools, combinations thereof, and/or the like. For example, the MIS port may be located on an upper part (e.g., the portion closer to the head of a patient) of a lower vertebral body (e.g., a lumbar vertebra). The positioning of the MIS port may then allow a surgical tool operated by a surgeon or a robot to have access to an entry point located in the upper part of the lower vertebral body to perform a surgery or surgical procedure on the lower vertebral body. The MIS port may be used both preoperatively (e.g., by an imaging device) and/or intraoperatively (e.g., by a surgical tool) to allow visual and/or physical access to the lower vertebral body.

The identified entry point may include or correspond to pose (e.g., position and orientation) information related to a surgical tool for performing a surgery or surgical procedure. For example, the identified entry point may specify or correspond to a specified pose of a surgical tool and/or components thereof (e.g., a distal end containing a drill bit) during the performance of the surgery or surgical procedure. The identified entry point may be determined by a system (e.g., a system 100) and/or components thereof (e.g., a processor 104) using one or more of a surgical plan, patient medical data, simulated images, and/or the like. The pose information may be used by a system (e.g., a system 100) and/or components thereof (e.g., a computing device 102) to align the imaging device relative to the identified entry point, thereby allowing the imaging device to capture images along the same trajectory that will be used by the surgical tool. The identified entry point may be determined by a surgeon based on a preoperative or surgical plan. In some embodiments, the identified entry point may be based on the location of an MIS port.

The method 200 also comprises receiving a second image depicting a second portion of the anatomical tissue around the identified entry point (step 212). The second image depicting the second portion of the anatomical tissue around the identified entry point may be captured, for example, by the imaging device (e.g., an imaging device 112) after being positioned near the identified entry point in the step 208. In some embodiments, the imaging device may be positioned based on the planned or actual pose and/or trajectory of the surgical tool and instructed (e.g., by a processor 104) to capture one or more images of the surface of the anatomical tissue. In some embodiments, the positioning of the imaging device capturing the second image may be known by the computing device 102, the processor 104, and/or one or more other components of the system 100 (e.g., a predetermined pose retrieved from a database, a pose determined and known by the computing device 102, etc.), which may enable the processor (e.g., the processor 104) executing the method 200 to know real-time the pose of the imaging device capturing the images. In some embodiments, the imaging device may be positioned or otherwise moved by a robot (e.g., a robot 114) or a component thereof (e.g., a robotic arm 116). The second image may be, for example, a CT scan, an MRI scan, or an ultrasound image. In some embodiments, the captured image may pass through an algorithm (e.g., an image processing algorithm 120) to filter the captured image (e.g., to remove artifacts) and/or to enhance the captured image (e.g., by enhancing a contrast between the anatomical tissue and the background). The captured image may depict a portion of the surface of the second portion of the anatomical tissue. For example, the anatomical tissue may be a vertebra, and the captured image may show a portion of the surface of the vertebra around an identified entry point. The captured image may be used by a system (e.g., a system 100) and/or components thereof (e.g., a computing device 102), stored in a database (e.g., a database 130), and/or shared with components external to the system via a cloud (e.g., a cloud 134). In some embodiments, the second portion of the anatomical tissue may be located proximate to the planned entry point. For instance, the second portion may be a known distance from the planned entry point. In still further embodiments, the second portion may appear as or be a prominent, distinct, or otherwise recognizable landmark, figure, shape, and/or shade at or proximate to the planned entry point in the captured image.

The method 200 also comprises comparing at least one feature of the second portion of the anatomical tissue around the identified entry point as depicted in the second image to at least one feature of the first portion of the anatomical tissue around the target entry point as identified in the first image (step 216). The comparison of the features may include using one or more algorithms (e.g., a comparison algorithm 126), and/or generating one or more overlays of the first image on the second image or vice versa. In some embodiments, the algorithm may identify differences (e.g., by comparing one or more features present in one or more of the images) between the first and second portions of the anatomical tissue. For instance, the comparison algorithm may process information associated with the one or more features such as one or more outlines, geometric forms, contours, surfaces, edges, gradients, combinations thereof, and/or the like associated with the first and second portions of the anatomical tissue as represented in the first and second images. In some embodiments, the algorithm may then provide a quantified degree of similarity (or difference) between the compared one or more features (e.g., a percent overlap of the one or more features in the one or more images, a statistical likelihood that the compared features are the same feature or a different feature, etc.) The quantified degree of similarity may be used in conjunction with a threshold to determine whether the first and second portions match. For example, in some embodiments the degree of similarity may be compared to a threshold and, when the degree of similarity exceeds the threshold (or in some cases falls below the threshold), a system (e.g., a system 100) may define the first and second portions as matching one another (e.g., the first and second portions share enough similarities or are close enough in appearance to one another to be defined as the same).

In some embodiments, one or more features associated with a surface of the anatomical tissue may be compared. For example, in embodiments where the anatomical tissue is a vertebra, the comparing of the anatomical tissue may include comparing the surface of the vertebra corresponding to the first portion of the vertebra depicted in the first image (e.g., the surface of the vertebra surrounding the target entry point of the vertebra) with the surface of the vertebra corresponding to the second portion of the vertebra depicted in the second image (e.g., the surface of the vertebra surrounding the identified entry point of the vertebra). In such embodiments, where the surfaces of the vertebra in the imaged first and second portions match, or are otherwise determined (e.g., based on a quantified degree of similarity)

to be the same, then the identified entry point may be confirmed to match the target entry point. Also, in some embodiments, the comparison of the surfaces may assist in verifying that a surgical tool (e.g., a surgical tool 140) is properly positioned to have a trajectory that matches a predetermined trajectory through the vertebra, which predetermined trajectory may have been selected to minimize the probability associated with, for example, bone surface skiving (e.g., the surgical tool puncturing the incorrect portion of the vertebra).

In some embodiments, the comparison of the one or more features may be based on, for example, gradient matching, surface detection, one or more surface angle comparisons, feature matching, combinations thereof, and/or the like. Gradient matching may be or comprise matching (e.g., aligning, overlaying, comparing, etc.) one or more gradients of the anatomical tissue as represented in the first image with one or more gradients of the anatomical tissue as depicted in the second image and determining a difference between the respective gradients. Surface detection may be or comprise detection of one or more surfaces associated with the anatomical tissue in the first image and detection of one or more surfaces associated with the anatomical tissue in the second image and, in some embodiments, comparing the respective surfaces to quantify a difference therebetween. Similarly, surface angle comparisons may be or comprise a comparison (e.g., to determine a degree of similarity or difference, etc.) between one or more angles of the identified or detected one or more surfaces of the anatomical tissue depicted in the two images. The feature matching may be or comprise a comparison of certain anatomical features (e.g., distinct landmarks, shapes, outlines, etc.) present in the anatomical tissue depicted in the two images. For example, the feature matching may be done by one or more algorithms (e.g., a comparison algorithm 126), which may take the two images and identify a specific anatomical landmark in the anatomical tissue in the first image and attempt to locate a corresponding anatomical landmark in the second image. The algorithm may determine a relative difference between the pose, shape, structure, outline, and/or contour of the anatomical landmark between the first image and the second image, and output, for example, a value based on the determined difference.

The method 200 also comprises generating a confirmation that the identified entry point matches the target entry point when the first portion matches the second portion (step 220). The confirmation may be based on the results of the comparison between the first and second portions of the anatomical tissue. For instance, if the comparison indicates that the one or more outlines, geometric forms, contours, surfaces, edges, gradients, combinations thereof, and/or the like of the first and second portions of the anatomical tissue match (e.g., are at the same location in a common coordinate system), the respective target entry point and identified entry point may be considered to also match (e.g., represent the same point on the anatomical tissue). The matching of the target entry point with the identified entry point may indicate to a system (e.g., a system 100), one or more components thereof, and/or a surgeon that the surgical tool is positioned to enter the anatomical tissue at the entry point identified in the anatomical plan.

In some embodiments, the method 200 may utilize a threshold for generating the confirmation. The threshold may be defined by the system, components thereof, and/or a surgeon and may indicate a degree of match between the target entry point and the identified entry point (based on an analysis of the surrounding first and second portions of anatomical tissue) sufficient to proceed with the surgery or surgical procedure. The confirmation may be sent to one or more components of a system (e.g., a system 100), which may determine whether or not the surgery or surgical procedure is cleared to proceed and may condition operation on receipt of the confirmation (e.g., a surgeon may wait for the confirmation before proceeding with surgery, a processor may prevent the activation of a surgical tool until receipt of the confirmation, etc.).

In some embodiments, the system may define a percent threshold (e.g., 99.9%, 99%, 98%, 97%, etc.) above which the system defines the identified entry point as matching the target entry point. For example, a threshold of 98% may indicate that, when 98% or more of the features of the first and second portions of the anatomical tissue are identical to each other, the target entry point and the identified entry point will be treated as the same and a confirmation (e.g., electronic signal) will be generated. In this example, any value falling below the 98% threshold will not return a confirmation, which may indicate that the target entry point and the identified entry point are not the same, at least to a desired degree of certainty (e.g., there is insufficient certainty that, if the surgical procedure were to proceed by entering the anatomical tissue with the surgical tool at the identified entry point, the surgical tool would be entering the anatomical tissue at the target entry point identified in a preoperative or surgical plan).

The method 200 also comprises causing the first image depicting the first portion of the anatomical tissue (e.g., the image received in the step 204) and the second image depicting the second portion of the anatomical tissue (e.g., the image received in the step 212) to be rendered to a user interface (step 224). The user interface (e.g., a user interface 110) may provide a visualization of the first and second portions of the anatomical tissue for visual comparison between the two. In some embodiments, the method 200 may make use of an algorithm (e.g., a transformation algorithm 124) to transform one or both of the images such that, when rendered to the user interface, both images display the same features relative to a single coordinate system. For example, if the second image of the second portion of the anatomical tissue is captured using an imaging device at an angle relative to the planned trajectory of the surgical tool, the algorithm may map, adjust, or otherwise change the depicted second portion of the anatomical tissue around the identified entry point to be shown from the same perspective as the first portion of the anatomical tissue to facilitate a visual comparison thereof. In some embodiments, the algorithm may use a transformation algorithm 124, such as a feature transformation function or algorithm (e.g., scale-invariant feature transform (SIFT)), to map the local features of one image to the other or vice versa. Also in some embodiments, the step 224 may comprise automatically annotating one or more features of the first portion of the anatomical tissue and one or features of the second portion of the anatomical tissue, whether to identify matching features and/or to identify distinguishing features between the two.

The user interface may allow a surgeon to view the two images for the purposes of confirming that the identified entry point matches the target entry point. In some embodiments, one of the two images may be overlaid on the other to better assist the surgeon with viewing the differences between the two images. In some embodiments, one or more of the two images may be rendered with metadata associated therewith (e.g., information about a quantified difference between the two images, information about an amount or degree by which the two images differ, etc.). The rendering of the two images may display each image with different visual indicia based on the type of tissue (e.g., soft tissue or hard tissue), based on the relative difference between the two images (e.g., a color gradient with a darker color representing a greater relative difference), based on the relative distance of the anatomical tissue from the entry point (e.g., greater contrast closer to the entry point), combinations thereof, and/or the like.

The present disclosure encompasses embodiments of the method 200 that comprise more or fewer steps than those described above, and/or one or more steps that are different than the steps described above.

The method 300 comprises receiving a surgical plan that defines a target entry point and one or more first features of anatomical tissue around a target entry point (step 304). The target entry point may be a designated location for entry into the anatomical tissue by a surgical tool. For example, where a spinal surgery will be undertaken to implant pedicle screws in a plurality of vertebrae, a target entry point may be identified on each vertebra, and a contour (and/or one or more other features) of the vertebra in an area surrounding the target entry point may be pictured, described, or otherwise identified in the surgical plan. The target entry point may be determined autonomously, by a surgeon or other user, and/or in part autonomously and in part with input of a surgeon or other user, and may be the preferred, ideal, or otherwise modeled/simulated entry point for a distal end (e.g., cutting end) of a surgical tool. The target entry point may vary depending on the type of surgery, available surgical tools, level of autonomy (e.g., manual, semi-autonomous, autonomous, etc.) associated with the surgery, and/or the like. For example, the target entry point may be on a surface of a bone, such as a vertebra. The target entry point may be associated with a particular trajectory, which trajectory may depend on information about the bone and/or information about the surgical tool being used. A particular trajectory associated with a given target entry point for a drill bit may be based, for example, on the type, size, and/or position of surgical drill bit used.

As noted above, the received surgical plan may illustrate or otherwise contain information about one or more first features of the anatomical tissue (e.g., a portion of a vertebra or other bone) around the target entry point. The one or more first features of the anatomical tissue may include one or more of an outline, geometric form, surface, edge, gradient, contour, and/or the like of the anatomical tissue around the target entry point. The surgical plan may depict, for example, an image of a varying amount of the anatomical tissue around the target entry point. For example, the image may depict a percentage of the anatomical tissue (e.g., 1%, 2%, 5%, 10%, 25%, 50%, 75%, 90%, 100%) surrounding the target entry point depending on, for example, surgical procedure, anatomical tissue type, and/or the like. In some embodiments, the anatomical tissue may be an organ and the image may depict only a portion thereof that is relevant to the surgical procedure. In some embodiments, the anatomical tissue may be located proximate to the target entry point. For instance, the anatomical tissue may be a known distance from the target entry point. In still further embodiments, the anatomical tissue may appear as or be a prominent, distinct, or otherwise recognizable landmark, figure, shape, and/or shade at or proximate to the target entry point in the received image.

In some embodiments, the surgical plan may contain one or more images of the anatomical tissue that may be captured preoperatively (e.g., before surgery), and may be stored in a system (e.g., a system 100) and/or one or more components thereof (e.g., a database 130, a memory 106, etc.). In some embodiments, the surgical plan may contain information related to a simulated anatomical tissue based on data obtained from preoperative imaging (e.g., a CT scan, an X-ray, etc.) and/or patient data (e.g., patient history).

In some embodiments, the anatomical tissue may be a vertebra, and the target entry point may be a location on the vertebra. The surgical plan may contain images of multiple surfaces of the vertebra and/or the immediate vicinity of the vertebra, or of the contour of the vertebra in the vicinity of the target entry point. As previously noted, the one or more images in the surgical plan may include renderings or computerized models of the anatomical tissue around the target entry point. In some embodiments, one or more algorithms may be used to generate an image of the anatomical tissue. The one or more algorithms may be artificial intelligence (AI) or machine learning (e.g., deep learning) algorithms that generate models of anatomical tissue after receiving as input, for example, patient medical records, type of planned surgical procedure, surgical instrumentation required for the surgical procedure, previously captured images or scans of the anatomical tissue (e.g., CT scans, X-rays, MM scans, ultrasound images, etc.), combinations thereof, and/or the like.

The method 300 also comprises positioning an imaging device near an identified entry point of the anatomical tissue (step 308). The positioning may comprise controlling a robotic arm (e.g., a robotic arm 116) to which the imaging device is attached. The imaging device may be any imaging device discussed herein (e.g., an imaging device 112), though the imaging device may be an imaging device not specifically mentioned herein. The imaging device may be controlled, navigated, or otherwise manipulated using a computing device such as a computing device 102, a processor such as a processor 104, a navigation system such as a navigation system 118, and/or combinations thereof. The imaging device may be oriented relative to an identified entry point of the anatomical tissue. For example, the imaging device may be aligned in a parallel orientation relative to a planned trajectory of a distal end of the surgical tool. In some embodiments, the imaging device may be oriented in the same pose as the surgical tool would be when performing the operation. In other words, the imaging device may be positioned such that the imaging device can capture images that depict a similar or the same trajectory as the distal end of the surgical tool when performing the surgery or surgical procedure relative to the identified entry point.

In some embodiments, the imaging device may be positioned partially or fully within the patient, an MIS port, and incision, combinations thereof, and/or the like. In one embodiment, the imaging device may be an ultrasound probe positioned within an MIS port, which in turn may be positioned within an incision. In this embodiment, the MIS port may be filled with a fluid (e.g., water, saline, combinations thereof, etc.) such that the fluid fills any otherwise empty space between the ultrasound probe and the imaged anatomical element, which may be necessary to obtain ultrasound images of the target entry point. The particular location of the MIS port is in no way limiting, and the MIS port may be constructed or otherwise provided on different areas of the patient depending on, for example, the type of surgery or surgical procedure being conducted, the availability of surgical tools, combinations thereof, and/or the like. For example, the MIS port may be located on an upper part (e.g., the portion closer to the head of a patient) of a lower vertebral body (e.g., a lumbar vertebra). The positioning of the MIS port may then allow a surgical tool operated by a surgeon or a robot to have access to an entry point located in the upper part of the lower vertebral body to perform a surgery or surgical procedure on the lower vertebral body. The MIS port may be used both preoperatively (e.g., by an imaging device) and/or intraoperatively (e.g., by a surgical tool) to allow visual and/or physical access to the lower vertebral body.

The identified entry point may include or correspond to pose (e.g., position and orientation) information related to a surgical tool for performing a surgery or surgical procedure. For example, the identified entry point may specify or correspond to a specified pose of a surgical tool and/or components thereof (e.g., a distal end containing a drill bit) during the performance of the surgery or surgical procedure. The pose information may be used by a system (e.g., a system 100) and/or components thereof (e.g., a computing device 102) to align the imaging device relative to the identified entry point, thereby allowing the imaging device to capture images along the same trajectory that will be used by the surgical tool (or a trajectory parallel to that trajectory). The identified entry point may be determined by a surgeon based on a preoperative or surgical plan. In some embodiments, the identified entry point may be based on the location of an MIS port.

The method 300 also comprises receiving a second image of one or more second features of the anatomical tissue around the identified entry point (step 312). The one or more second features may be or include one or more of an outline, geometric form, surface, edge, gradient, contour, and/or the like of the anatomical tissue around the identified entry point. The second image depicting one or more second features of the anatomical tissue around the identified entry point may be captured by an imaging device (e.g., an imaging device 112) after being positioned near the identified entry point in step 308. In some embodiments, the imaging device may be positioned based on the planned or actual pose and/or trajectory of the surgical tool and instructed (e.g., by a processor 104) to capture one or more images of the surface of the anatomical tissue. The image capture may be, for example, a CT scan, an MRI scan, or an ultrasound image. In some embodiments, the second image may pass through an algorithm (e.g., an image processing algorithm 120) to filter the captured image (e.g., to remove artifacts) and/or enhance the captured image (e.g., by enhancing a contrast between the anatomical tissue and the background). The captured image may depict the surface of anatomical tissue. For example, the anatomical tissue may be a vertebra, and the captured image may show a surface of the vertebra around an identified entry point. The captured image may be used by a system (e.g., a system 100) and/or components thereof (e.g., a computing device 102), stored in a database (e.g., a database 130), and/or shared with components external to the system via a cloud (e.g., a cloud 134).

The method 300 also comprises determining whether the one or more first features match the one or more second features and quantifying any one or more differences between the one or more first features and the one or more second features (step 316). The method 300 may make use of one or more algorithms (e.g., a comparison algorithm 126) to compare the one or more first features with the one or more second features and determine whether they are identical or not. Where the one or more first features are not identical to the one or more second features, the method 300 may make use of one or more algorithms (e.g., a quantification algorithm 122) to produce a quantity reflecting a difference between the one or more first features and the one or more second features. For instance, the algorithm may receive the results of the comparison between relative positions of the one or more first features and the one or more second features and may base the quantification on the compared positions. The quantified difference may be percent-based (e.g., 0.01% difference, 0.05% difference, 0.1% difference, 0.5% difference, 1% difference, etc.). In some embodiments, the percent-based difference may be based on the percentage of each of one or more first features that matches (e.g., lines up with, overlaps, shares the same coordinates, etc.) with a respective each of the one or more second features. The percent-based difference may use weighted averages if reporting the percent-based differences for multiple features and may additionally or alternatively report percent-based differences for each feature found used when quantifying the difference between the two sets of features. In some embodiments, a 100% difference may indicate that the one or more first features of the anatomical tissue share no common features, no reference points, and/or no overlap with the one or more second features. In some embodiments, the quantified difference may be a positional or angular difference (e.g., 0.1 mm difference, 0.2 mm difference, 0.5 mm difference, 1 mm difference, 0.1 degree difference, 0.2 degree difference, 1 degree difference, etc.). The positional difference may be based on a relative coordinate difference between the one or more first features and the corresponding one or more second features in one or more directions and/or in one or more angles (e.g., positional and/or angular differences along the length, width, and/or height of the surface of the anatomical tissue). The type and number of features compared are in no way limited, and various features may be compared by the method 300. Examples of features include, but are in no examples include way limited to, one or more gradients (e.g., of one or more surfaces) and/or one or more anatomical landmarks (e.g., shapes, outlines, and/or forms depicted in the first and/or second image).

The method 300 also comprises generating a confirmation that the identified entry point matches the target entry point when the one or more first features match the one or more second features (step 320). The confirmation may be generated even when the result of the step 316 is a quantification of one or more differences between the one or more first features and the one or more second features if, for example, the quantified difference does not exceed (or falls below, as appropriate) a predetermined threshold. In other words, if 95% similarity between the first features and the second features is required to yield a determination that the one or more first features match the one or more second features, then a quantification showing a 96% similarity between the one or more first features and the one or more second features would be sufficient to yield a match determination, which would in turn result in generating a confirmation that the identified entry point matches the target entry point.

In some embodiments, the step 320 may be the same as or similar to the step 220 of the method 200. The generating may also comprise operating a system (e.g., a system 100) and/or one or more components thereof (e.g., a surgical tool 140) based on the received confirmation. For instance, the system and/or the one or more components thereof may be configured to not proceed with the surgical procedure, or at least the surgical task involving entering the anatomical tissue, until the confirmation is received. In some embodiments, the method 300 may perform the step 320 simultaneously or nearly simultaneously with a step involving generating an alert (e.g., see step 324 below). In such embodiments, the system and/or one or more components thereof may be configured to receive either one of the confirmation or the alert and may operate differently based on the received signal (e.g., based on whether the system or component receives the confirmation or the alert). For example, a surgical tool 140 may be instructed (e.g., controlled by a processor) to await receipt of the confirmation or an alert before drilling into the anatomical tissue. The surgical tool 140 may be locked, idled, or may otherwise fail to drill or apply power to the drill bit until a confirmation is received.

The method 300 also comprises generating an alert that the identified entry point does not match the target entry point when the one or more first features do not match the one or more second features (step 324). The alert may be based on the quantification between the anatomical tissue around the target entry point and the anatomical tissue around the identified entry point. For example, if the quantification indicates that one or more features of the anatomical tissue around the identified entry point and respective one or more features of the anatomical tissue around the target entry point do not match (e.g., a predetermined threshold for identifying a match has not been met), the identified entry point and the target entry point may not match. The alert may be sent to a system (e.g., a system 100) and/or one or more components thereof (e.g., a computing device 102) to indicate that the identified entry point and the target entry point may not match. The alert may also indicate to the system, components thereof, a surgeon, and/or the like that the surgical tool is not correctly aligned with the target entry point. The alert may be an audible alert, a visual alert, or a combination thereof.

As discussed above, in some embodiments, the method 300 may implement a threshold, below which the alert is generated. The threshold may be a percent threshold (e.g., 99%, 95%, 90%, etc.) for the percent quantification below which the system determines that the identified entry point and the target entry point do not match and generates the alert. For example, with a threshold of 95%, any quantification below 95% results in the system generate the alert. In this example, the threshold below 95% may indicate that the identified entry point and the target entry point do not match to a degree of confidence appropriate for permitting the surgery or surgical procedure to continue (e.g., a similarity or match of at 95%). In some embodiments, the generation of the alert may limit certain functions of the system (e.g., a system 100) on a temporary basis. For instance, the generation of the alert may limit or lock the use of a surgical tool (e.g., a surgical tool 140) until the alert is overridden. In this example, the surgeon may be capable of manually overriding the lock on the surgical tool.

The method 300 also comprises performing a surgical procedure on the anatomical tissue using a surgical tool (step 328). A surgical tool (e.g., a surgical tool 140) may be aligned with the identified entry point at a planned trajectory (which may be, for example, parallel to or identical to a trajectory at which the image of the step 312 was taken) and, upon receipt of a confirmation (e.g., an indication that the identified entry point matches the target entry point), activate to drill, ream, tap, shave, or otherwise cut into the anatomical tissue. In some embodiments, the surgical tool may be positioned near or in an MIS port. The surgical tool may be positioned in the MIS port such that the distal end of the surgical tool is capable of contacting the anatomical tissue, while the proximal end does not enter the patient. In some embodiments, the surgical tool may be attached to a robot (e.g., a robot 114) and/or robotic arms such as robotic arms 116 that may conduct or assist with the surgery or surgical procedure in accordance with a surgical plan. In some embodiments, the surgical tool may not begin the surgical procedure (or at least the surgical task involving entering the anatomical tissue) until a confirmation (e.g., a signal indicating that the target entry point matches the identified entry point, as generated in the step 320) is received by the system and/or components thereof. In one embodiment, the surgical tool may drill into a vertebra. The trajectory of the surgical tool may be parallel to a trajectory of the imaging device during the steps 308 and/or 312 of the method 300. In other words, the trajectory of the surgical tool may be a trajectory that has been confirmed to match a predetermined trajectory identified, for example, in the surgical plan of the step 304. The surgical tool may drill into the vertebra to insert screws (e.g., pedicle screws); to insert fiducials (e.g., devices capable of being used with imaging techniques such as fluoroscopy to capture additional patient information); to relieve pressure; to prepare the patient for additional surgeries, surgical procedures, or surgical tasks; combinations thereof; and/or for any for any other purpose. The confirmation code may indicate to the surgical tool (e.g., to a processor within or controlling the surgical tool) that the surgical tool is correctly aligned with the target entry point to reduce the probability of negative consequences associated with an incorrect tool alignment such as tool skiving, drilling at an incorrect angle, excess cutting or drilling through the anatomical material, and/or the like.

The present disclosure encompasses embodiments of the method 300 that comprise more or fewer steps than those described above, and/or one or more steps that are different than the steps described above.

As noted above, the present disclosure encompasses methods with fewer than all of the steps identified in FIGS. 2 and 3 (and the corresponding description of the methods 200 and 300), as well as methods that include additional steps beyond those identified in FIGS. 2 and 3 (and the corresponding description of the methods 200 and 300). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for verifying a bone entry point, the method comprising:

receiving, by a processor, a surgical plan that defines a target bone entry point and a first portion of a bone surface at least partially surrounding the target bone entry point;

positioning, by the processor, an imaging device near an identified bone entry point and along a planned bone entry trajectory of a surgical tool;

receiving, at the processor and from the imaging device, an image of a second portion of the bone surface at least partially surrounding the identified bone entry point;

comparing, by the processor, at least one feature of the first portion to at least one feature of the second portion to quantify a degree of similarity therebetween;

generating, by the processor when the quantified degree of similarity between the first portion and the second portion exceeds a threshold, a confirmation;

verifying, by the processor and when the confirmation is generated, the planned bone entry trajectory;

causing the imaging device to move away from the identified bone entry point;

causing, when the planned bone entry trajectory is verified, the surgical tool to move into a position to align with the planned bone entry trajectory; and performing, by the processor and when the planned bone entry trajectory is verified, a surgical step with the surgical tool along the planned bone entry trajectory.

2. The method of claim 1, wherein the confirmation indicates that the identified bone entry point matches the target bone entry point.

3. The method of claim 1, wherein performing the surgical step comprises causing the surgical tool to drill into the identified bone entry point along the planned bone entry trajectory.

4. The method of claim 1, wherein each of the at least one feature of the first portion and the at least one feature of the second portion is a surface gradient.

5. The method of claim 1, wherein each of the at least one feature of the first portion and the at least one feature of the second portion is an anatomical landmark.

6. The method of claim 1, wherein the confirmation indicates a level of statistical certainty that the identified bone entry point matches the target bone entry point.

7. The method of claim 1, wherein the threshold is a percent similarity between the at least one feature of the first portion and the at least one feature of the second portion.

8. The method of claim 7, wherein the threshold is at least ninety-nine percent.

9. The method of claim 1, wherein the imaging device is an ultrasound probe.

10. The method of claim 1, wherein the imaging device is positioned in a surgical incision.

11. The method of claim 10, the surgical incision comprises an MIS port.

12. A system for verifying an entry point into anatomical tissue, the system comprising:

a processor; and a memory storing instructions for execution by the processor that, when executed by the processor, cause the processor to:

receive a surgical plan that defines a target entry point of an anatomical tissue and comprises a first image of a first portion of the anatomical tissue near the target entry point;

cause an imaging device to be positioned proximate to an identified entry point of the anatomical tissue and along a planned bone entry trajectory of a surgical tool;

receive, from the imaging device, a second image of a second portion of the anatomical tissue near the identified entry point;

cause the first image and the second image to be rendered to a user interface;

compare the first portion to the second portion to quantify a difference between at least one characteristic of the first portion of the anatomical tissue and at least one characteristic of the second portion of the anatomical tissue;

cause the imaging device to move away from the identified entry point; and cause the surgical tool to move into a position to align with the planned bone entry trajectory.

13. The system of claim 12, wherein the imaging device is positioned in a surgical incision.

14. The system of claim 13, wherein the surgical incision comprises an MIS port.

15. The system of claim 12, wherein the instructions further cause the processor to:

generate, when the quantified difference between the at least one characteristic of the first portion of the anatomical tissue and the at least one characteristic of the second portion of the anatomical tissue is below a threshold value, a confirmation that the identified entry point matches the target entry point;

verify, when the confirmation is generated, the planned bone entry trajectory; and perform, when the planned bone entry trajectory is verified, a surgical step with the surgical tool along the planned bone entry trajectory.

16. A system comprising:

an imaging device;

a processor; and a memory storing instructions for execution by the processor that, when executed by the processor, cause the processor to:

receive a surgical plan that defines a target bone entry point and a first bone contour proximate the target bone entry point;

position the imaging device near an identified bone entry point and along a planned bone entry trajectory of a surgical tool;

cause the imaging device to capture an image of a second bone contour proximate the identified bone entry point;

determine, based on a predetermined threshold, whether the first bone contour matches the second bone contour;

when the first bone contour matches the second bone contour, generate a confirmation that the identified bone entry point matches the target bone entry point;

when the first bone contour does not match the second bone contour, generate an alert that the identified bone entry point does not match the target bone entry point;

cause the imaging device to move away from the identified bone entry point; and cause, when the confirmation is generated, the surgical tool to move into a position to align with the target bone entry point.

17. The system of claim 16, wherein the imaging device is an ultrasound probe.

\* \* \* \* \*